(12) United States Patent
Takeuchi et al.

(10) Patent No.: US 8,491,709 B2
(45) Date of Patent: Jul. 23, 2013

(54) ACTIVE OXYGEN GENERATING DEVICE, HUMIDIFIER, AND AIR PURIFICATION SYSTEM WITH HUMIDIFIER

(75) Inventors: Shiro Takeuchi, Tokyo (JP); Akira Shiga, Tokyo (JP); Takuya Furuhashi, Tokyo (JP)

(73) Assignee: Mitsubishi Electric Corporation, Chiyda-Ku, Tokyo (JP)

(*) Notice: Subject to any disclaimer, the term of this patent is extended or adjusted under 35 U.S.C. 154(b) by 345 days.

(21) Appl. No.: 12/922,955

(22) PCT Filed: Mar. 3, 2009

(86) PCT No.: PCT/JP2009/053930
§ 371 (c)(1),
(2), (4) Date: Sep. 16, 2010

(87) PCT Pub. No.: WO2009/128297
PCT Pub. Date: Oct. 22, 2009

(65) Prior Publication Data
US 2011/0017066 A1    Jan. 27, 2011

(30) Foreign Application Priority Data
Apr. 14, 2008 (JP) ................. 2008-104396

(51) Int. Cl.
*B03C 3/47* (2006.01)
(52) U.S. Cl.
USPC .......... 96/22; 95/6; 95/77; 96/26; 96/41; 96/69; 96/94; 204/212; 204/213; 261/92

(58) Field of Classification Search
USPC ........ 96/26, 39, 41, 42, 94, 18–24, 69; 95/77, 95/2–7; 204/212, 213; 261/69.1, 92
See application file for complete search history.

(56) References Cited

U.S. PATENT DOCUMENTS

| | | | | |
|---|---|---|---|---|
| 2,307,603 A | * | 1/1943 | Penney | 96/41 |
| 2,486,877 A | * | 11/1949 | Ransburg et al. | 96/42 |
| 2,663,380 A | * | 12/1953 | Savitz | 96/41 |

(Continued)

FOREIGN PATENT DOCUMENTS

| | | |
|---|---|---|
| CN | 86 1 03146 A | 12/1986 |
| CN | 2165143 Y | 5/1994 |

(Continued)

OTHER PUBLICATIONS

German Office Action dated Mar. 27, 2012, issued in the corresponding German Patent Application No. 11 2009 000 921.2, and a English Translation thereof. (13 pages).

(Continued)

*Primary Examiner* — Richard L Chiesa
(74) *Attorney, Agent, or Firm* — Buchanan Ingersoll & Rooney PC

(57) ABSTRACT

To provide a small active oxygen generating device capable of efficiently continuously generating active oxygen while supplying oxygen in the air. In the active oxygen generating device in which water is made to exist between an anode and a cathode composed of a base material containing a conductive polymer and by turning on electricity between the anode and the cathode, the conductive polymer deoxidizes the oxygen dissolved in the water to generate active oxygen, the cathode is rotatably installed about a conductive horizontal axis with part of the surface being projected over the surface of the water.

20 Claims, 3 Drawing Sheets

U.S. PATENT DOCUMENTS

| | | | |
|---|---|---|---|
| 3,912,467 A * | 10/1975 | Trump et al. ............... | 96/94 |
| 4,769,138 A * | 9/1988 | Frandsen ................ | 210/150 |
| 4,773,978 A | 9/1988 | Thomassen et al. | |
| 5,429,669 A * | 7/1995 | Chang ...................... | 96/51 |
| 5,741,887 A | 4/1998 | Morita et al. | |
| 6,845,971 B2 * | 1/2005 | Bachert ..................... | 261/37 |
| 6,958,088 B1 * | 10/2005 | Moriyama ................ | 96/39 |
| 2006/0275651 A1 * | 12/2006 | Furuta et al. ............... | 429/45 |

FOREIGN PATENT DOCUMENTS

| | | | |
|---|---|---|---|
| EP | 1 887 287 A2 | | 2/2008 |
| JP | 60-177614 A | * | 9/1985 |
| JP | 9-175801 | | 7/1997 |
| JP | 10-081985 A | | 3/1998 |
| JP | 10-099863 A | | 4/1998 |
| JP | 11-079708 A | | 3/1999 |
| JP | 2001-026892 A | | 1/2001 |
| JP | 2002-273433 A | | 9/2002 |
| JP | 2006-299326 A | | 11/2006 |
| JP | 2008-081760 A | | 4/2008 |

OTHER PUBLICATIONS

International Search Report (PCT/ISA/210) issued on Apr. 14, 2009, by Japanese Patent Office as the International Searching Authority for International Application No. PCT/JP2009/053930.

Notification of the First Office Action issued by the Chinese Patent Office on Oct. 9, 2012 in corresponding Chinese Application No. 200980112684.1, and an English translation thereof.

Notice of Reasons for Rejection issued by the Japanese Patent Office on Jan. 8, 2013 in corresponding Japanese Application No. 2010-508135, and an English translation thereof.

* cited by examiner (a)

(b)

(a)

(b)

(a)

(b)

ACTIVE OXYGEN GENERATING DEVICE, HUMIDIFIER, AND AIR PURIFICATION SYSTEM WITH HUMIDIFIER

TECHNICAL FIELD

The present invention relates to an active oxygen generating device, and more particularly to an active oxygen generating device capable of obtaining means that efficiently continuously generates active oxygen with a simple structure.

BACKGROUND ART

Conventionally, as means that generates active oxygen to disinfect harmful microorganisms and various bacteria in water, methods using such as discharging and photocatalyst are known. However, the former discharge method consumes a great deal of electrical energy and is required to secure security against a high-voltage input, which being problematic. The latter photocatalyst method has problems that in order to obtain effects, a ultra-violet optical source is necessary, so that the device becomes large and irradiation to a human body is harmful. A method that generates active oxygen by electrolysis using electricity in water can be found as well, however, hydrogen and chlorine occur as byproducts and may explode and generate an irritating smell disadvantageously. As means to solve these problems, means that generates active oxygen is known by turning on electricity between an anode and a cathode that is made to support a conductive polymer having an active oxygen generating ability (hereinafter, denoted as a conductive polymer). (For example, refer to Patent Document 1)
Patent Document 1 Japanese Unexamined Patent Application Publication No. H10-99863 (claim 1, claim 9, FIG. 1)

SUMMARY OF INVENTION

Problems to be Solved by the Invention

For example, a conductive polymer such as polyaniline has an outstanding oxidation-reduction reaction. The conductive polymer provides dissolved oxygen in water with electrons and deoxidizes oxygen to generate active oxygen. When electrons are continuously provided by giving an electrically deoxidizing potential to polyaniline having such an oxidation-reduction ability, active oxygen continues to be generated in water. However, since the content of the dissolved oxygen in water is limited, active oxygen production decreases as dissolved oxygen is consumed. When used for a long period, active oxygen production decreases as impurities are attached on the surface of the electro-conductive polymer.

The present invention is made in consideration of the above problems and its purpose is to provide a small active oxygen generating device capable of efficiently continuously generating active oxygen while supplying oxygen in the air.

Means for Solving the Problems

In the active oxygen generating device according to the present invention, water is made to exist between an anode and a cathode composed of a base material containing a conductive polymer. By turning on electricity between the anode and the cathode, the conductive polymer deoxidizes the oxygen dissolved in the water. The cathode is rotatably installed about a horizontal axis with part of the surface being projected over the surface of the water.

Effect of the Invention

Since a water film is created at the upper part of the cathode by the rotation of the cathode made of a base material containing the conductive polymer, the active oxygen generating device according to the present invention can take in oxygen in the air from the interface between the water film and the air. Therefore, while actively continuously supplying oxygen in the air, the device can react to electrons provided by the conductive polymer to efficiently continuously generate active oxygen.

DESCRIPTIONS OF CODES AND SYMBOLS

Figure 1:
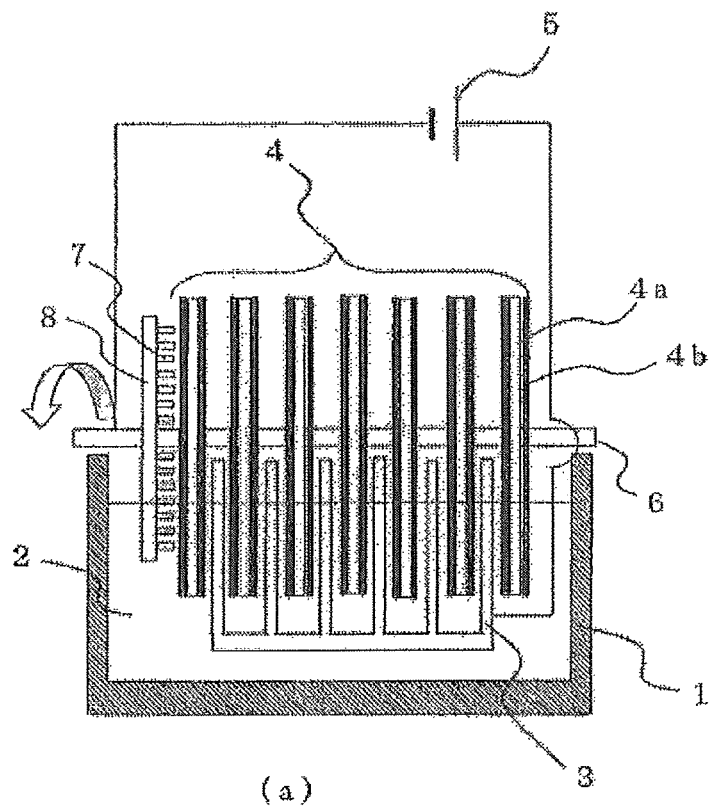
FIG. 1 is a side view (a) and an elevation view (b) of the active oxygen generating device according to Embodiment 1 of the present invention.
Figure 1:
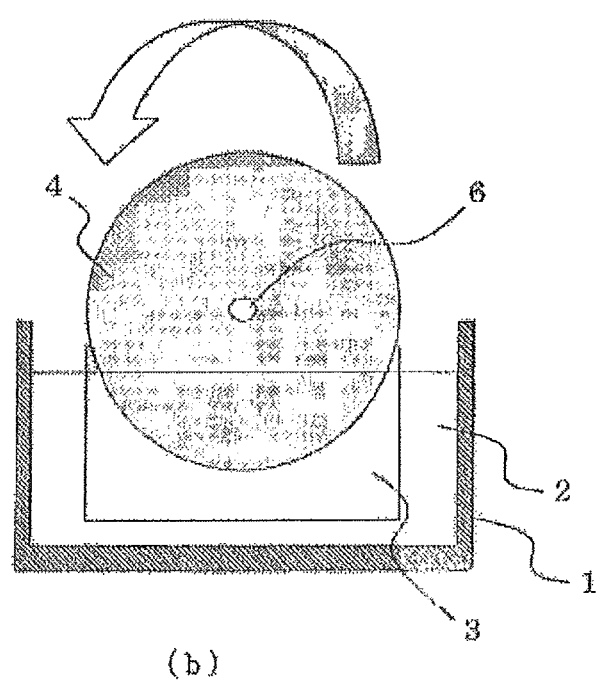
Figure 2:
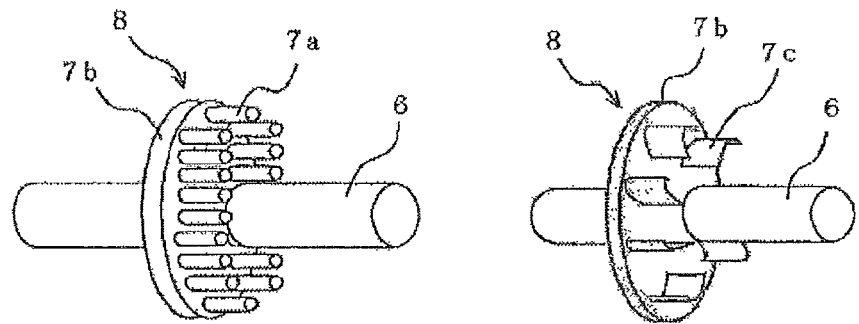
FIG. 2 is a perspective view showing rotor, which is dissolved oxygen improvement means in the water, according to Embodiment 1 of the present invention.

1 water tank
2 water
3 anode
4 cathode
4*a* conductive base material
4*b* conductive polymer
5 DC power supply
6 rotation axis
6*a* support shaft
7 projection portion
7*a* rod-like projection
7*b* disk
7*c* vane
8 rotor

DESCRIPTION OF THE PREFERRED EMBODIMENTS

Embodiment 1
Descriptions will be given to Embodiment 1 of the present invention using FIG. 1 as follows. FIG. 1(*a*) is a side view of an active oxygen generating device according to Embodiment 1 of the present invention. FIG. 1(*b*) is an elevation view.

The active oxygen generating device is composed of a water tank 1, an anode 3 which is installed so as to be partially or totally immersed into the water 2 of the water tank 1, a cathode 4 which is made of a base material 4*a* containing a conductive polymer 4*b* and oppositely placed against the anode 3 with a predetermined interval, and a DC power supply 5 such as a battery connected with the anode 3 and the cathode 4. By turning on the electricity between the anode 3 and the cathode 4, the conductive polymer 4*b* is adapted to deoxidize oxygen dissolved in the water 2 between both electrodes to generate active oxygen. That is, by the conductive polymer 4*b* contained on the surface of the cathode 3, electrons are supplied to the oxygen dissolved in the water and active oxygen such as superoxide, hydroxy radical, and hydrogen peroxide is generated.

Here, in Embodiment 1, the anode 3 is composed of a plurality of rectangular conductive plate interlinked in a comb-tooth fashion. The cathode 4 is a disciform conductive base material 4a with the conductive polymer 4b being applied, adhered, or impregnated and supported on the surface, having a configuration in which at the center of a plurality of disk conductive base materials 4a, a conductive rotation axis 6 is inserted and interconnected. Each disciform cathode 4 is disposed between comb-tooth like anodes 3. While the lower part of the cathode 4 is buried under the surface of water, the upper part is disposed to extrude over the surface of the water.

Therefore, when the cathode 4 is made to rotate about the rotation axis 6, since a water film is formed on the surface of the cathode 4, oxygen is continuously taken in from the interface of the water film and the air. That is, oxygen is allowed to be supplied into the water. Then, since the water film is always formed at the upper part of the cathode 4 which is projected from the surface of the water, the rotation speed of the cathode 4 is adjusted so that the water film does not get dry.

Active oxygen production is dependent on the area immersed in water, so that the larger the immersed area, the better. The immersed part preferably has a structure always to be exposed to the air by the rotation.

Thus, by making the conductive rotation axis 6 to be the conduction part of the cathode 4, no slide part exists in the contact point of the cathode 4 and the conduction part, so that a wear-free contact point by rotation is achieved. By making the center of rotation to be a conduction part, there is no need of considering the twist of wiring by rotation as well. Further, by making a configuration such that only the cathode 4 rotates and the anode 3 is separated to be immersed in water, a degree of freedom for arrangement increases and method of wiring and applying current becomes easy.

For the conductive polymer 4b used for the cathode 4, at least one material is selected for use among commonly known polyaniline, polyaniline derivative, polypyrrole, polythiophene, and polyacetylene. The lower resistance of the conductive base material 4a, the better, and the surface resistance may preferably be $10^{-3}$ to $10^3$ Ω/sq. Such an infinitesimal voltage as almost no electrolysis occurs in water is applied in the present active oxygen generating device, therefore, when the surface resistance is high, a large voltage drop occurs at the most distant point from the current-carrying part of the electrode, resulting in almost no voltage application. Here, Ω/sq. represents a surface resistance, denoting a resistance of the surface of 1 cm$^2$ of the subject to be measured.

Blowing means, not shown, may preferably be provided so that the surface of the cathode 4 is actively exposed to the air. By sending the air to the surface of the cathode, much more oxygen can be taken into the water film formed thereon, contributing to increase active oxygen production. As mentioned above, when providing blowing means, by installing a rotor 8 having a plurality of projection portions 7 so as to move in and over the water on the rotation axis 6, the projection portions 7 can rotate the rotation axis 6 by taking advantage of the force of the wind. The projection portions 7 are set on the rotation axis 6 almost in parallel or radially. Such a configuration enables the cathode 4 to rotate without a driving power source, achieving a small size and energy saving of the device.

The conductive base material 4a of the cathode 4 may be formed by fabric cloth and mesh texture besides a disciform, increasing active oxygen production because of a wider surface area. It may be formed by a porous material such as foam, allowing to take in as much oxygen in the air into the water in the hollow portion inside the base material at the time of rotation. In Embodiment 1, the conductive polymer of the cathode is supposed to contain the base material, however, an insulation material is allowable when the conductive polymer is applied or impregnated on the surface of the base material.

As means to retain much dissolved oxygen in water, the water temperature may be adjusted at 0 to 30° C. The lower the water temperature, the more the amount of the dissolved oxygen, therefore, the low water temperature is kept to be below by disposing a Peltier element and a condenser in the water tank 1 or so as to contact therewith. The water temperature is adjusted to be within the above range because water freezes below 0° C. and when 30° C. or over, the dissolved oxygen concentration is reduced by half compared with 0° C.

As mentioned above, by providing projection portions 7 that continuously move in and over the water on the rotation axis 6, oxygen in the air is taken in when the projection portions 7 move from over the water to in the water to increase the dissolved oxygen in the water, so that active oxygen generated on the surface of the cathode increases. The projection portions 7 that are means for increasing the dissolved oxygen in the water may preferably be a projection having a large surface area such that a plurality of rod-like projections 7a are provided on the disk 7b to form a brush-shaped rotor 8 or a plurality of vanes 7c are provided as protrusions on the disk 7b to form a waterwheel-shaped rotor 8.

Embodiment 2

Figure 3:
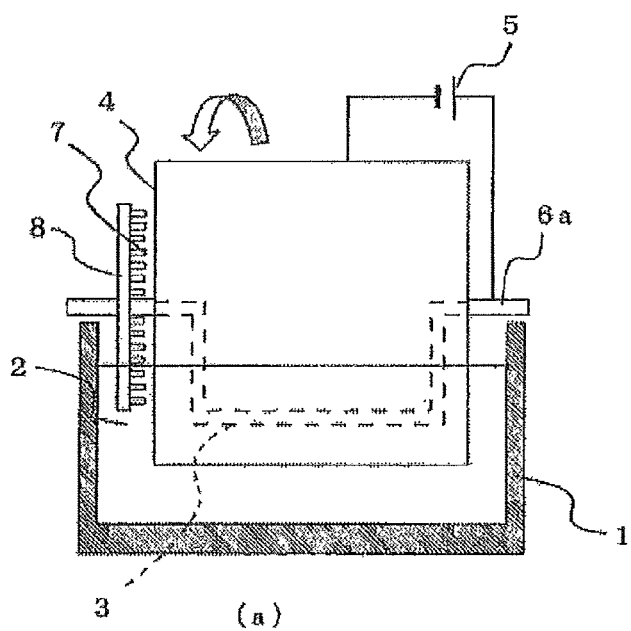
FIG. 3 is a side view (a) and an elevation view (b) of the active oxygen generating device according to Embodiment 2 of the present invention.
Figure 3:
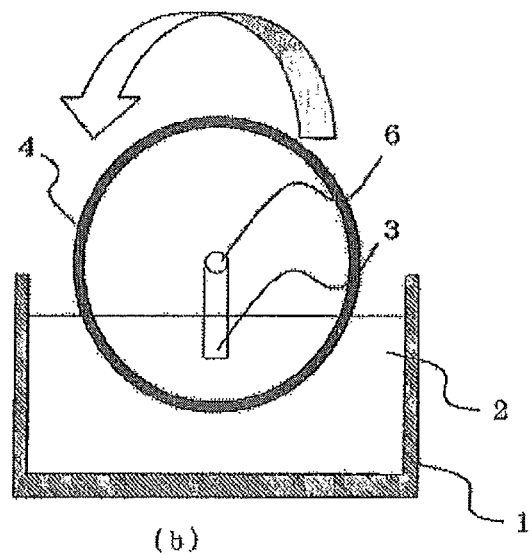

Descriptions will be given to Embodiment 2 of the present invention using FIG. 3 as follows. FIG. 3(a) is a side view of the active oxygen generating device according Embodiment 2 of the present invention, and FIG. 3(b) is an elevation view.

Embodiment 2 has a configuration such that a cylindrical or a drum-shaped base material 4a containing the conductive polymer 4b is made to be the cathode 4, a rod-like conductive base material disposed so as to penetrate the center of the cathode is made to be the anode 3, and active oxygen is generated with part (lower part) of the circumference surface being immersed in the water while the cathode 4 rotates, with the upper part of the circumference surface being over the water face, and with electricity being turned on between the cathode and the anode 3. The anode 3 has a concavely bent structure so that a part opposing the cathode 4 is immersed in the water. That is, the anode 3 is a support shaft 6a of the cathode 4 to be a fixed axis. The cathode 4 and the rotor 8 are supported so as to freely rotate about the support shaft 6a (anode 3). In order to electrically insulate the cathode 4 from the support shaft (anode 3), a bush made of such as resin is interposed at the boss part of the cathode 4. The cathode 4 rotates by a motor, not shown, via such as gears.

Such a configuration enables to secure a wide area of the cathode 4 immersed in the water against the volumetric capacity of the device to allow much active oxygen production. The anode 3 can be formed with a small area, achieving a simple structure.

Embodiment 3

Figure 4:
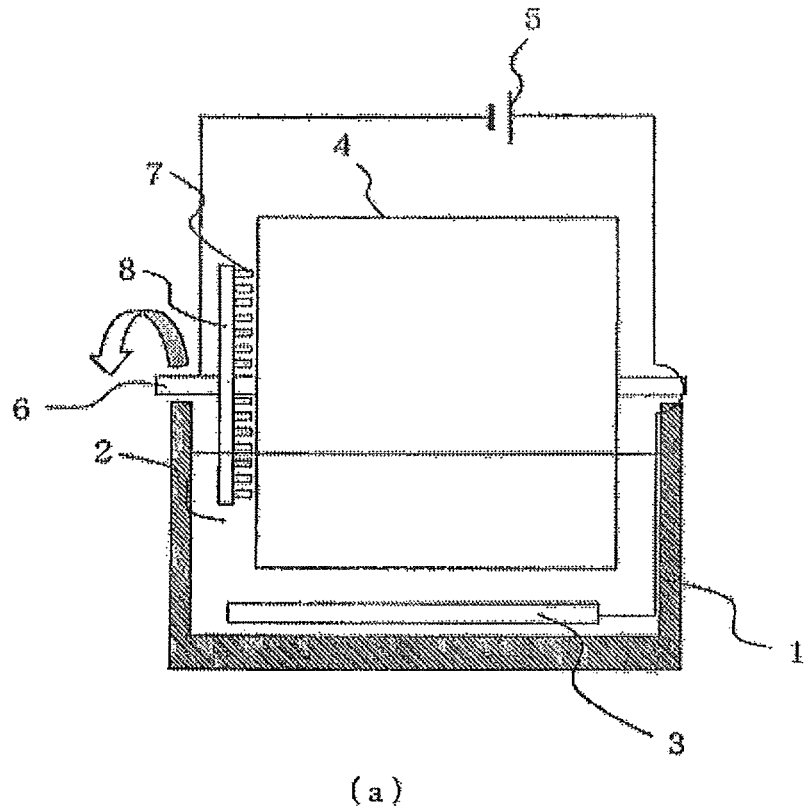
FIG. 4 is a side view (a) and an elevation view (b) of the active oxygen generating device according to Embodiment 3 of the present invention.
Figure 4:
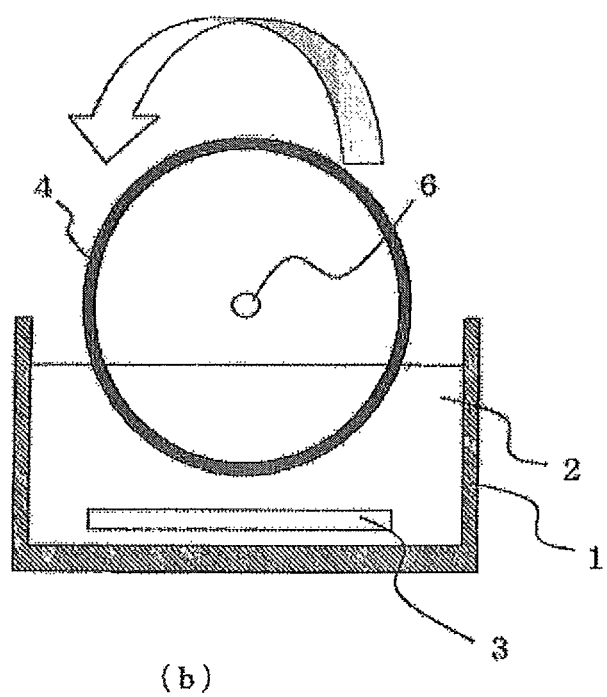

Descriptions will be given to Embodiment 3 using FIG. 4 as follows. FIG. 4(a) is a side view of the active oxygen generating device according Embodiment 3 of the present invention, and FIG. 4(b) is an elevation view.

Embodiment 3 has a configuration such that a cylindrical or a drum-shaped base material 4a containing the conductive polymer 4b is made to be the cathode 4, and active oxygen is generated with part (lower part) of the circumference surface being immersed in the water while the cathode 4 rotates, with the upper part of the circumference surface being over the water face, and with electricity being turned on between the cathode and the anode 3 disposed at the bottom face of the water tank 1 under the cathode 4.

Such a configuration enables to secure a wide area of the cathode 4 immersed in the water against the volumetric capacity of the device to allow much active oxygen production. A distance of 1 to 20 mm is enough between the anode 3 and the cathode 4. The arrangement of the anode 3 can be changed according to an installation location. Since the cathode 4 and the anode 3 are separated, a method of turning on electricity between both electrodes becomes easy.

In the above-mentioned Embodiments 1 to 3, dirt attached on the surface of the electrode according to use may disturb an electric current flow to cause an excessive voltage to be applied. When a high voltage is applied, a reference voltage is changed to reduce active oxygen production because hydrogen generation becomes dominant instead of active oxygen. The cathode and the anode may come into contact according to the use to cause an excess current. When the excess current is applied to the conductive polymer contained in the cathode, a phenomenon may occur in which no electron is provided from the electro-conductive polymer, and ignition may be caused due to the application of the excess current. Therefore, by providing means, not shown, that detect an electric current and voltage applied between the cathode and the anode to suspend electricity between both electrodes at the time of detecting an abrupt increase in the current and the voltage, a mechanism (control means) that prevent the above-mentioned phenomenon may be preferable.

By turning on the electricity between electrodes mentioned above, at least hydrogen and chlorine are generated along with active oxygen. Hydrogen may be piled up to explode. Chlorine may also do harm to the human body because it is an poisonous gas. Therefore, a mechanism (control means) may be preferable that adjusts or suspends the electricity between electrodes when concentration of the above gases increases by providing gas detection means, not shown, on the water.

Safety as a device can be enhanced by providing such a mechanism (control means) with the device.

With the configuration of the active oxygen generating device shown in the above each embodiment, active oxygen can be efficiently continuously generated while supplying oxygen in the air. Since active oxygen has a function to disinfect harmful microorganisms and various bacteria in water, the present active oxygen generating device has an antibacterial and an odor prevention effects when installed into a humidifier and an air purification system having a humidifier to enable to retain sanitation of the device.

The invention claimed is:

1. An active oxygen generating device in which water is made to exist between an anode and a cathode composed of a base material containing a conductive polymer and by turning on electricity between the anode and the cathode, the conductive polymer deoxidizes oxygen dissolved in the water to generate active oxygen, comprising:
   dissolved oxygen increasing means that takes in oxygen in the air into the water to increase the dissolved oxygen in the water, wherein
   the cathode is rotatably installed about a rotation axis with part of the surface being projected over the surface of the water,
   the dissolved oxygen increasing means includes a rotor having a plurality of projection portions, and
   the rotor is rotatably provided about the rotation axis with part of the rotor being projected over the surface of the water.

2. The active oxygen generating device of claim 1, wherein the cathode has a conductive rotation axis for conduction as the rotation axis.

3. The active oxygen generating device of claim 1, wherein the cathode is composed of a plurality of disks, or a single cylinder or a drum.

4. The active oxygen generating device of claim 1, wherein the conductive polymer of the cathode is composed of at least one material selected from among polyaniline, polyaniline derivative, polypyrrole, polythiophene, and polyacetylene.

5. The active oxygen generating device of claim 1, wherein the base material of the cathode including the conductive polymer is composed of a material having a surface resistance of $10^{-3}$ to $10^3$ Ω/sq.

6. The active oxygen generating device of claim 5, wherein the base material of the cathode including the conductive polymer is composed of a porous material.

7. The active oxygen generating device of claim 1, wherein blowing means that rotates the cathode is provided.

8. The active oxygen generating device of claim 1, wherein a temperature of the water is retained at 0 to 30° C. in which the cathode and the anode are immersed.

9. The active oxygen generating device of claim 1, wherein the plurality of projection portions are provided on the rotation axis so as to move under and over the water surfaces.

10. The active oxygen generating device of claim 9, wherein the projection portions are set radially about the rotation axis or almost in parallel with the rotation axis via the rotor.

11. The active oxygen generating device of claim 1, wherein detection means that detect an abnormality of a conducting current and control means that suspends electricity between the anode and the cathode when the detection means detects the abnormality of operations.

12. The active oxygen generating device of claim 11, wherein the detection means detects an electric current or a voltage between the anode and the cathode.

13. The active oxygen generating device of claim 12, wherein the detection means detects the concentration of hydrogen or chlorine generated by conduction between the anode and the cathode.

14. A humidifier or an air purification system having a humidifier, wherein the active oxygen generating device of claim 1 is mounted.

15. The active oxygen generating device of claim 2, wherein the cathode is composed of a plurality of disks, or a single cylinder or a drum.

16. The active oxygen generating device of claim 2, wherein the conductive polymer of the cathode is composed of at least one material selected from among polyaniline, polyaniline derivative, polypyrrole, polythiophene, and polyacetylene.

17. The active oxygen generating device of claim 3, wherein the conductive polymer of the cathode is composed of at least one material selected from among polyaniline, polyaniline derivative, polypyrrole, polythiophene, and polyacetylene.

18. The active oxygen generating device of claim 2, wherein
 the base material of the cathode including the conductive polymer is composed of a material having a surface resistance of $10^{-3}$ to $10^3$ $\Omega$/sq.

19. The active oxygen generating device of claim 3, wherein
 the base material of the cathode including the conductive polymer is composed of a material having a surface resistance of $10^{-3}$ to $10^3$ $\Omega$/sq.

20. The active oxygen generating device of claim 4, wherein
 the base material of the cathode including the conductive polymer is composed of a material having a surface resistance of $10^{-3}$ to $10^3$ $\Omega$/sq.

\* \* \* \* \*